United States Patent [19]

Sprecker et al.

[11] Patent Number: 5,358,930
[45] Date of Patent: Oct. 25, 1994

[54] 2-ETHOXY-4-FORMYL PHENYL ESTER OF PROPIONIC ACID AND USE IN AUGMENTING OR ENHANCING THE AROMA OF PERFUME COMPOSITIONS, COLOGNES AND PERFUMED ARTICLES

[75] Inventors: Mark A. Sprecker, Sea Bright; Richard A. Weiss, Pine Brook; Richard M. Boden, Ocean; Olivier J. Gillotin, Denville, all of N.J.

[73] Assignee: International Flavors & Fragrances Inc., New York, N.Y.

[21] Appl. No.: 168,349

[22] Filed: Dec. 17, 1993

[51] Int. Cl.$^5$ .................................................. A61K 7/46
[52] U.S. Cl. ...................................... 512/21; 560/144; 252/174.11; 252/8.6
[58] Field of Search ..................... 512/21; 560/144; 252/174.11, 86

[56] References Cited

U.S. PATENT DOCUMENTS

| | | | |
|---|---|---|---|
| 2,774,791 | 12/1956 | Alt | 512/21 |
| 4,512,919 | 4/1985 | Wilson et al. | 252/522 R |
| 4,515,987 | 5/1985 | Boden et al. | 512/21 |
| 4,657,700 | 4/1987 | Ochsner | 560/144 |

OTHER PUBLICATIONS

Allured Publishing Company, "Flavor And Fragrance Materials", 1993, published by Allured Publishing Company; front title page; p. 114 and p. 276 made of record.

*Primary Examiner*—James H. Reamer
*Attorney, Agent, or Firm*—Arthur L. Liberman

[57] ABSTRACT

Described is 2-ethoxy-4-formyl phenyl ester of propionic acid of our invention defined according to the structure:

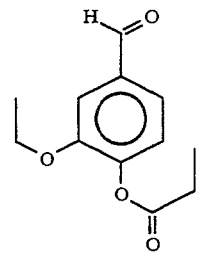

and uses thereof in augmenting or enhancing the aroma of perfume compositions, perfumed articles and colognes.

12 Claims, 3 Drawing Sheets

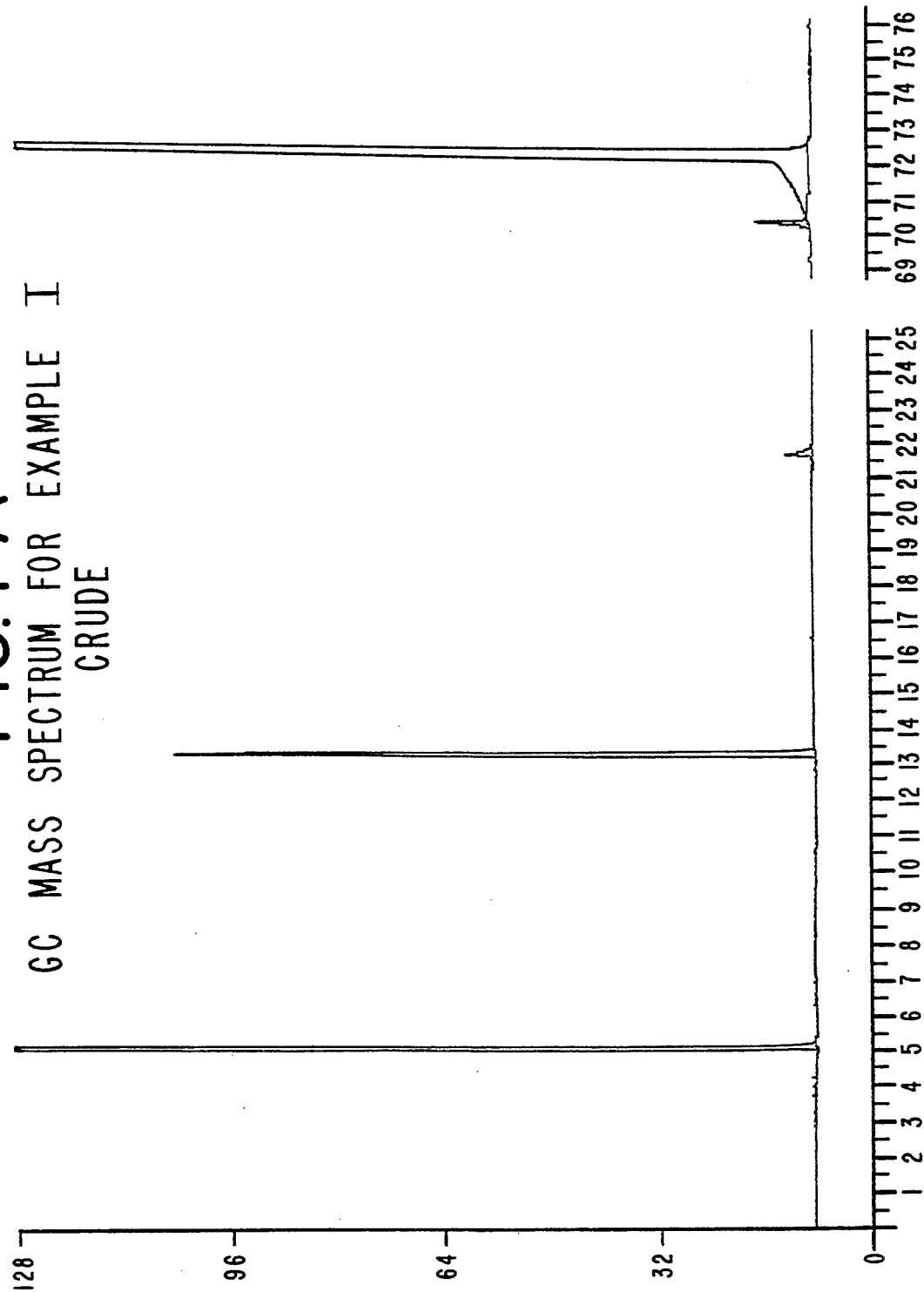

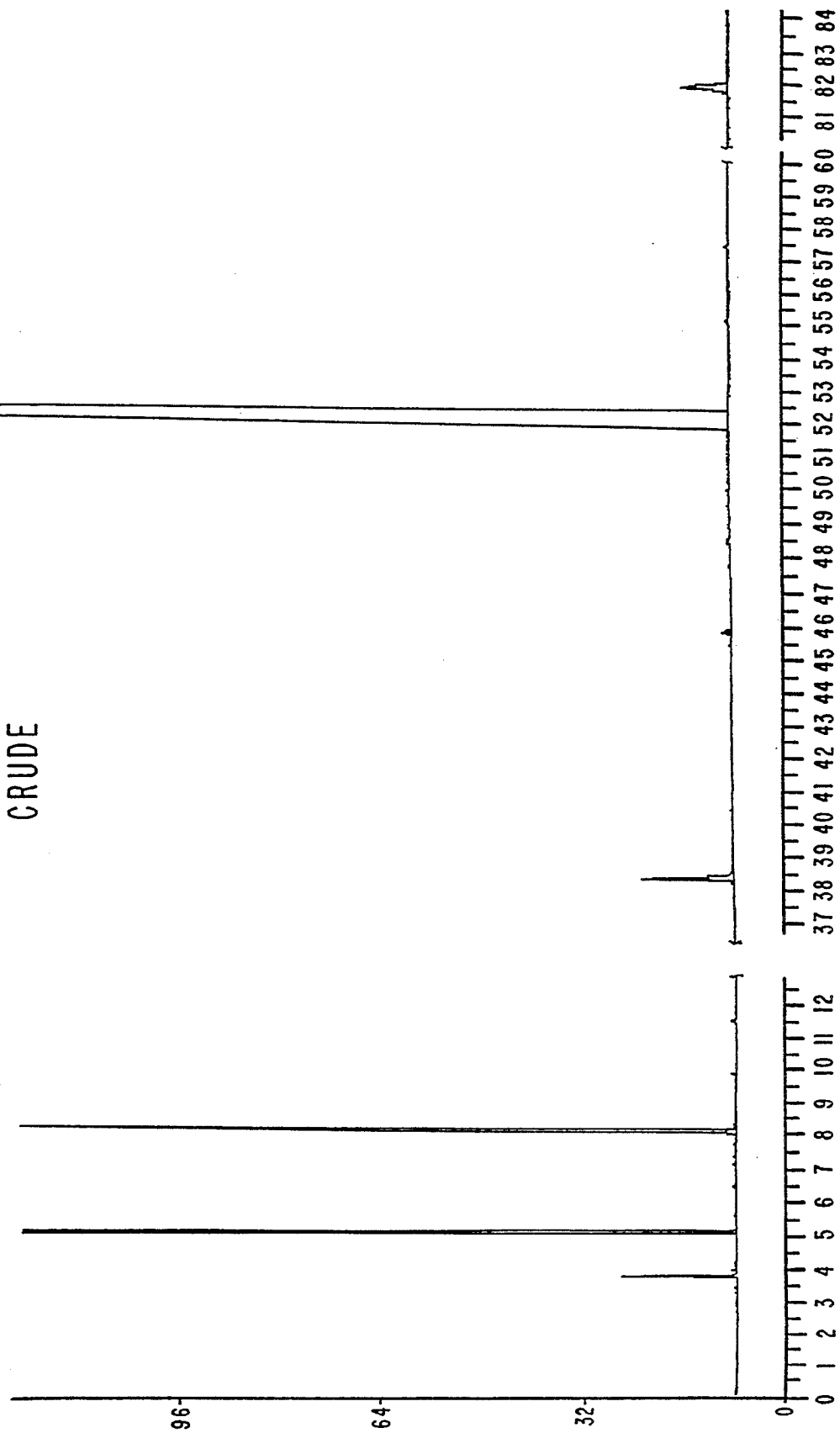
FIG.I-B
GC MASS SPECTRUM FOR EXAMPLE I CRUDE

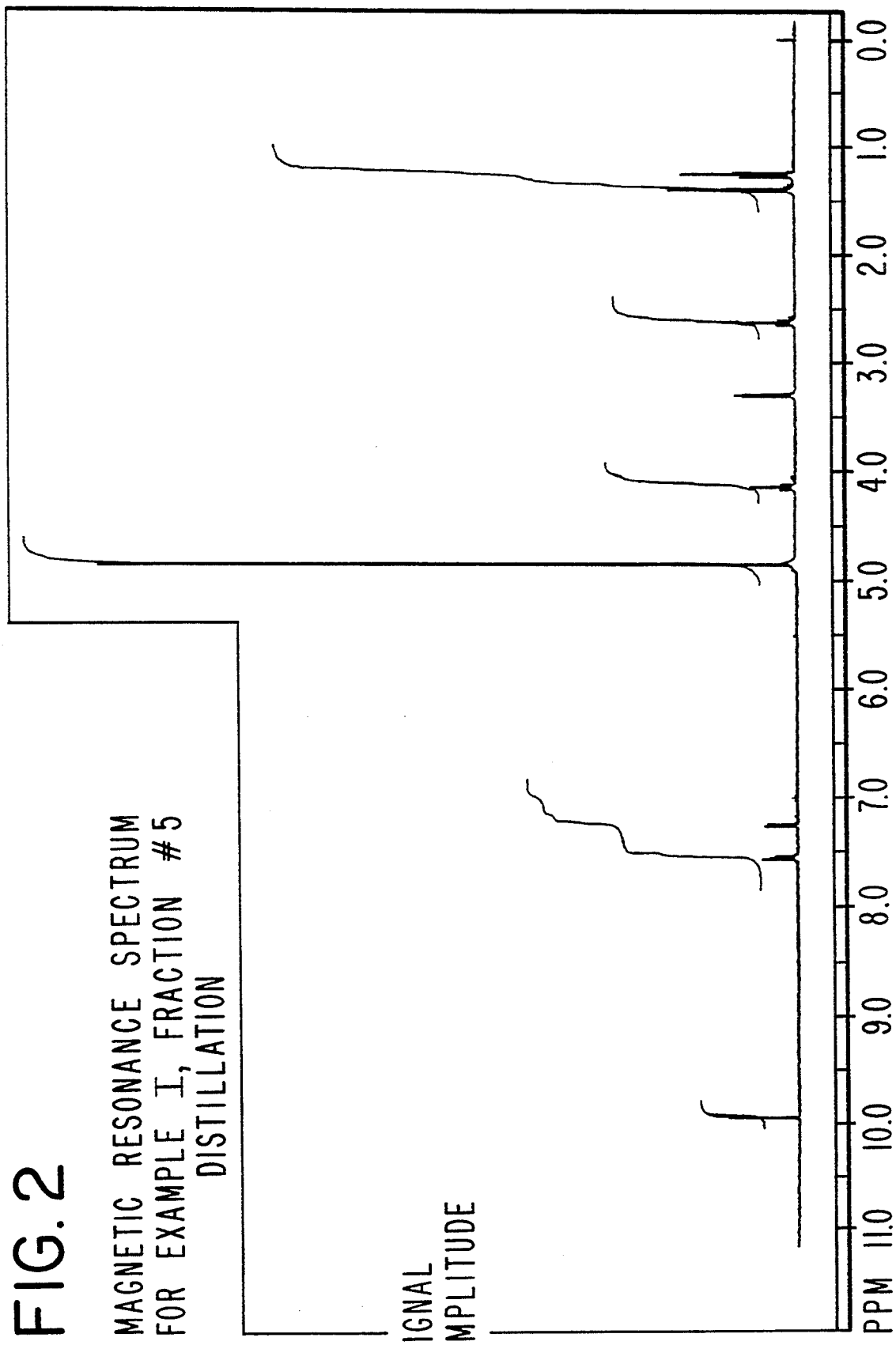
FIG. 2 MAGNETIC RESONANCE SPECTRUM FOR EXAMPLE I, FRACTION #5 DISTILLATION

2-ETHOXY-4-FORMYL PHENYL ESTER OF PROPIONIC ACID AND USE IN AUGMENTING OR ENHANCING THE AROMA OF PERFUME COMPOSITIONS, COLOGNES AND PERFUMED ARTICLES

BACKGROUND OF THE INVENTION

The present invention relates to 2-ethoxy-4-formyl phenyl ester of propionic acid of our invention defined according to the structure:

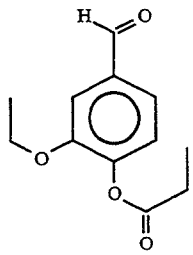

and uses thereof in augmenting or enhancing the aroma of perfume compositions, colognes and perfumed articles (including solid or liquid anionic, cationic, nonionic or zwitterionic detergents, fabric softener compositions and fabric softener articles, cosmetic powders, hair preparations and perfumed polymers).

There has been considerable work performed relating to substances which can be used to impart (augment or enhance) fragrances (to) or (in) various consumable materials. These substances are used to diminish the use of natural materials some of which may be in short supply and to provide more uniform properties in the finished product. In addition, there is a need to use in such consumable materials perfume materials which are non-discoloring.

Rich, natural vanilla bean and sweet aromas with dark chocolate topnotes are highly desirable for many uses in perfume compositions, perfumed articles and colognes particularly where a "sweet" note is needed to be added to musk formulations and citrusy formulations.

Esters of various vanilla derivatives are known in the prior art and furthermore are known to be useful in flavors and fragrances. Thus, vanillin acetate having the structure:

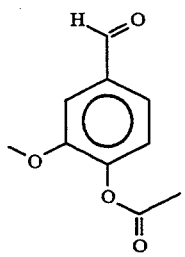

is described by Nunomura, et al in Agric. Biol. Chem. 44 (2), 39–351 (at page 345) to be a flavor component in the acetic fraction of Shoyu (soy sauce). Furthermore, the vanillin acetate having the structure:

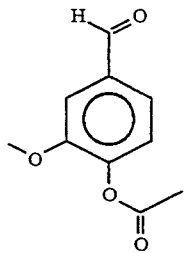

and vanillin isobutyrate having the structure:

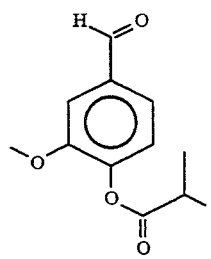

as well as ethyl vanillin acetate having the structure:

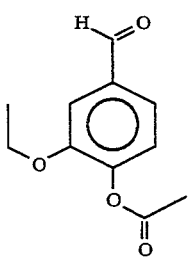

are disclosed in "Flavor And Fragrance Materials", 1993 published by the Allured Publishing Company. Vanillin acetate is given F.E.M.A. No. (Flavor Extract Manufacturers Association Number) 3108; vanillin isobutyrate is given F.E.M.A. No. 3754. Ethyl vanillin acetate however is only given C.A.S. No. 72207-94-4 at page 114 of "Flavor And Fragrance Materials", 1993, published by Allured Publishing Company.

Nothing in the prior art however discloses or infers the unobvious, unexpected organoleptic qualities of 2-ethoxy-4-formyl phenyl ester of propionic acid of our invention defined according to the structure:

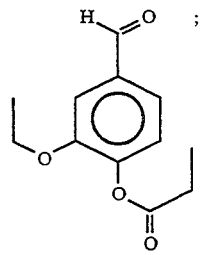

and 2-ethoxy-4-formyl phenyl ester of propionic acid of our invention defined according to the structure:

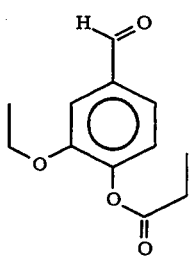

is not disclosed in the literature and is a novel material.

BRIEF DESCRIPTION OF THE DRAWINGS

FIG. 1A is the GC spectrum for the crude reaction product of Example I containing the compound having the structure:

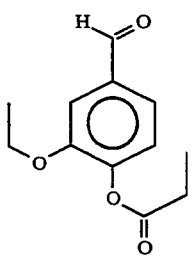

(Conditions: 50 meter×0.32 mm carbowax 20M column programmed from 75°–250° C. at 2° C. per minute).

FIG. 1B is the GC spectrum for the crude reaction product of Example I containing the compound having the structure:

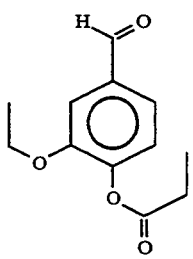

(Conditions: 50 meter×0.32 mm bonded methyl silicone column programmed from 75°–250° C. at 2° C. per minute).

FIG. 2 is the magnetic resonance spectrum for distillation Fraction 5 of the distillation of the reaction product of Example I for the compound having the structure:

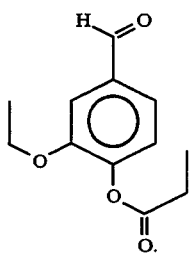

THE INVENTION

It has now been discovered that novel solid and liquid perfume compositions, colognes and perfumed articles having rich, natural vanilla bean, sweet aromas with dark chocolate topnotes may be provided by the use of 2-ethoxy-4-formyl phenyl ester of propionic acid of our invention having the structure:

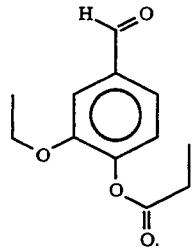

The 2-ethoxy-4-formyl phenyl ester of propionic acid of our invention having the structure:

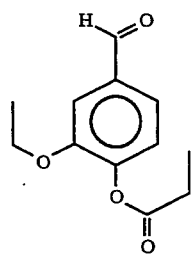

may be produced by first reacting ethyl vanillin having the structure:

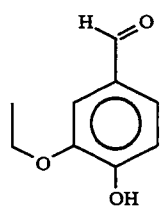

with propionic anhydride according to the reaction:

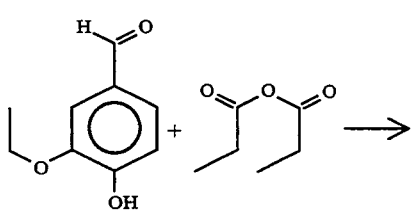

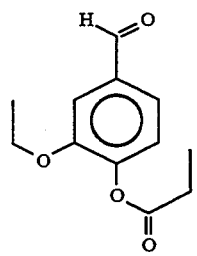

thereby producing 2-ethoxy-4-formyl phenyl ester of propionic acid of our invention having the structure:

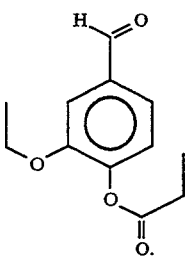

The mole ratio of propionic anhydride:ethyl vanillin may vary from about 2.5:2 up to about 5:2 with a preferred mole ratio of propionic anhydride:ethyl vanillin of about 3:2.

The reaction temperature is preferably at reflux conditions (e.g., 129° C. at atmospheric pressure). Preferably the reaction is carried out at atmospheric pressures, however the reaction can be carried out at super atmospheric pressures, (e.g., greater than one atmosphere, that is, from about 1 up to about 10 atmospheres) and at temperatures greater than 129° C. (e.g., 130°-180° C.).

At the end of the reaction, the reaction mass is neutralized with such materials as aqueous sodium hydroxide or sodium carbonate or sodium bicarbonate and then dried. The reaction mass is then distilled on a fractionation column yielding fractions which are rich in the compound having the structure:

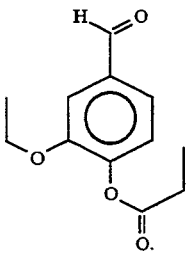

The 2-ethoxy-4-formyl phenyl ester of propionic acid of our invention having the structure:

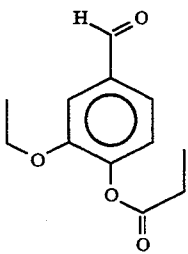

is capable of augmenting or enhancing or imparting rich, natural vanilla bean and sweet aromas with dark chocolate topnotes; and at the same time is non-discoloring in perfume compositions (as compared with other vanillin derivatives).

The 2-ethoxy-4-formyl phenyl ester of propionic acid of our invention and one or more auxiliary perfume ingredients including, for example, alcohols, aldehydes, ketones, nitriles, esters other than the 2-ethoxy-4-formyl phenyl ester of propionic acid of our invention, cyclic esters (lactones), dialkyl ethers, alkyl alkenyl ethers, thioethers, thiols, carboxylic acids and hydrocarbons and natural essential oils and synthetic essential oils may be so admixed so that the combined odors of the individual components produce a pleasant and desired fragrance particularly and preferably in the natural citrusy or musky area. Such perfume compositions usually contain (a) the main note or the "bouquet" or the foundation stone of the composition; (b) modifieres which round off and accompany the main notes; (c) fixatives which include odorous substances which lend a particular note to the perfume throughout all stages of evaporation and substances which retard evaporation; and (d) topnotes which are usually low-boiling, fresh-smelling materials.

In perfume compositions, it is the individual components which contribute to their particular olfactory characteristics; however, the overall sensory effect of the perfume composition will be at least the sum total of the effect of each of the ingredients. Thus, the 2-ethoxy-4-formyl phenyl ester of propionic acid of our invention can be used to alter, modify, impart or enhance the aroma characteristics of or to a perfume composition, for example, by utilizing or moderating the ol-factory reactions contributed by another ingredient in the composition.

The amount of 2-ethoxy-4-formyl phenyl ester of propionic acid of our invention which will be effective in perfume compositions as well as in perfumed articles and colognes depends on many factors, including the other ingredients, their amounts and the effects which are desired. It has been found that perfume compositions containing as little as 0.01% of the 2-ethoxy-4-formyl phenyl ester of propionic acid of our invention or even less (e.g., 0.005%), can be used to impart a very natural, substantive, rich, natural vanilla bean and sweet aroma with dark chocolate topnotes to soaps, cosmetics and other products. The amount employed can range up to 70% of the fragrance components and will depend on considerations of cost, nature of the end product, the effect desired on the finished product and the particular fragrance sought.

The 2-ethoxy-4-formyl phenyl ester of propionic acid of our invention is useful (taken alone or taken together with other ingredients in perfume compositions) as (an) olfactory component(s) in detergents and soaps, space odorants and deodorants, perfumes, colognes, toilet waters, bath preparations such as lacquers, brilliantines, pomades and shampoos; cosmetic preparations such as creams, deodorants, hand lotions and sun screens; powders such as talcs, dusting powders, face powders and perfumed article compositions of matter such as perfumed polypropylene, polyethylene and polyurethanes, particularly long-lasting or partially short-lasting mixtures of, for example, encapsulated perfumes suspended in free perfume compositions and the like.

When used as (an) olfactory component(s), as little as 0.1% of the 2-ethoxy-4-formyl phenyl ester of propionic acid of our invention will suffice to impart an intense non-discoloring rich, natural vanilla bean and sweet aroma with dark chocolate topnotes. Generally, no more than 3% of the 2-ethoxy-4-formyl phenyl ester of propionic acid of our invention based on the ultimate end product is required in the perfume composition.

In addition, the perfume composition or fragrance composition of our invention can contain a vehicle or carrier for the 2-ethoxy-4-formyl phenyl ester of propionic acid of our invention. The vehicle can be a liquid such as a non-toxic alcohol (e.g., ethyl alcohol), a non-toxic glycol (e.g., propylene glycol or 1,2-butylene glycol or sorbitol) or the like. The carrier can also be an absorbent solid such as a gum (e.g., gum arabic, xanthan gum, guar gum or the like) or components for encapsulating the material (such as gelatin or ethyl cellulose as by coacervation).

When used as a component of a perfumed article such as a perfumed plastic or solid or liquid anionic, cationic, nonionic or zwitterionic detergent or a drier-added fabric softener article or fabric softener composition or a shampoo or a soap, the range of 2-ethoxy-4-formyl phenyl ester of propionic acid of our invention useable varies from 0.005% up to about 5% by weight of the perfumed article. The lower range of this range, e.g., 0.005% up to 0.1% of the 2-ethoxy-4-formyl phenyl ester of propionic acid of our invention is most preferred when using it in a drier-added fabric softener article or fabric softener composition in view of the need for a "non-perfumy" but pleasant head space aroma above the batch of clothes dried using the drier-added fabric softener article or fabric softener composition in a standard automatically operated tumble drier.

It will thus be apparent that the 2-ethoxy-4-formyl phenyl ester of propionic acid of our invention can be utilized to augment, alter and modify or enhance sensory properties particularly organoleptic properties of a wide variety of consumable materials.

The following examples are illustrative and the invention is to be considered to be restricted thereto only as indicated in the appended claims. Example I sets forth a process for producing the 2-ethoxy-4-formyl phenyl ester of propionic acid of our invention. Example II, et seq., set forth the organoleptic utilities of the 2-ethoxy-4-formyl phenyl ester of propionic acid of our invention.

All parts and percentages given herein are by weight unless otherwise specified.

EXAMPLE I

Preparation of 2-ETHOXY-4-FORMYL Phenyl Ester of Propionic Acid

Reaction:

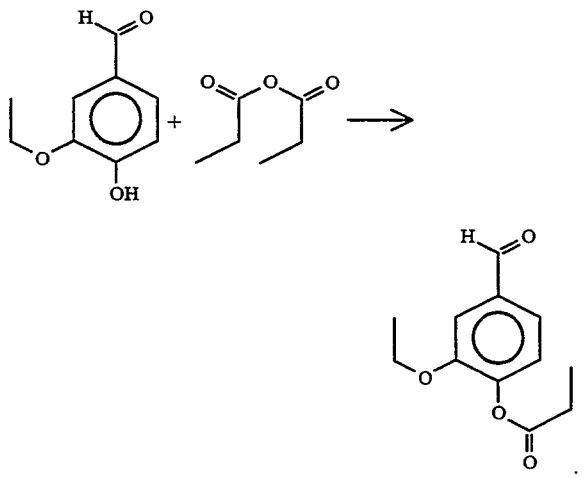

Into a 2 liter reaction flask equipped with stirrer, thermometer, reflux condenser and heating mantle are placed 332 grams of ethyl vanillin (2.0 moles); 300 ml toluene and 390 grams (3.0 moles) or propionic anhydride.

The reaction mass is heated to reflux (129° C.) with stirring and maintained at reflux for a period of one hour. At the end of the one hour period, 100 grams additional propionic anhydride is added and the reaction is continued at reflux for a period of three hours with stirring. At the end of the three hour period, the reaction mass is cooled.

With stirring, the reaction mass is admixed (quenched) with 500 ml of 5% aqueous sodium hydroxide at 25° C.

The reaction mass is then washed with two volumes of water and the organic phase is separated from the aqueous phase.

The reaction mass is then "rushed over" at 155° C. and 1 mm/Hg. pressure.

The reaction mass is then fractionally distilled yielding the following fractions:

| Fraction No. | Vapor Temp. (°C.) | Liquid Temp. (°C.) | Vacuum mm/Hg. Pressure |
|---|---|---|---|
| 1 | 69/42 | 23/109 | 12.0/3.0 |
| 2 | 31 | 125 | 2.0 |
| 3 | 154 | 158 | 0.8 |
| 4 | 155 | 158 | 0.85 |
| 5 | 157 | 168 | 0.85 |
| 6 | 151 | 210 | 0.8. |

FIGS. 1A and 1B are GC spectra for the crude reaction product prior to distillation.

FIG. 2 is the magnetic resonance spectrum for distillation Fraction 5.

The resulting product has an intense and substantive rich, natural vanilla bean, sweet aroma with dark chocolate topnotes.

EXAMPLE II

Fragrance Formulations

To demonstrate the use of the 2-ethoxy-4-formyl phenyl ester of propionic acid of our invention prepared according to Example I, in magnolia, musk and citrusy formulations the following formulae are prepared:

| | Parts by Weight | | |
|---|---|---|---|
| Ingredients | II(A) | II(B) | II(C) |
| Phenylethyl alcohol | 200 | 25 | 25 |
| Geraniol | 400 | 25 | 25 |
| Trichloromethylphenyl carbinyl acetate | 20 | 5 | 5 |
| Phenylethyl acetate | 60 | 5 | 5 |
| Undecylenic aldehyde (10% in diethyl phthalate) | 5 | 0 | 0 |
| n-Nonyl aldehyde (10% in diethyl phthalate) | 2 | 0 | 0 |
| Musk ketone | 10 | 150 | 20 |
| Musk ambrette | 10 | 150 | 20 |
| Eugenyl phenyl acetate | 20 | 5 | 5 |
| Citronellol | 100 | 100 | 400 |
| Vanillin (10% in diethyl phthalate) | 6 | 6 | 6 |
| Eugenol | 30 | 5 | 5 |
| Citronellyl formate | 30 | 5 | 5 |
| Geranyl acetate | 10 | 5 | 5 |
| Linalool | 40 | 20 | 20 |
| Geranyl phenyl acetate | 50 | 20 | 20 |
| Cis-beta, Gamma-hexenyl acetate | 2 | 0 | 0 |
| 1-(2,5,5-Trimethyl-1,3-cyclo-hexadien-1-yl)-1,3-butanedione | 5 | 5 | 5 |
| Farnesene isomer mixture produced according to Example I of U.S. Letters Patent No. 4,394,444 (the specification for which is incorporated by reference herein) | 60 | 60 | 40 |
| 2-Ethoxy-4-formyl phenyl ester of propionic acid | 120 | 120 | 120 |

-continued

| Ingredients | Parts by Weight | | |
|---|---|---|---|
| | II(A) | II(B) | II(C) |
| having the structure: | | | |

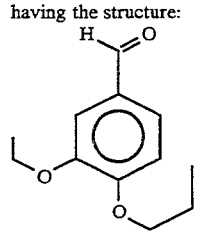

produced according
to Example I, supra.

The addition of 2-ethoxy-4-formyl phenyl ester of propionic acid of our invention to each of the formulations of Examples II(A), II(B) and II(C) adds to these fragrances intense rich, natural vanilla bean and sweet undertones with dark chocolate topnotes.

Accordingly, the perfume composition of Example II(A) can be described as "a magnolia aroma with rich, natural vanilla bean and sweet undertones and dark chocolate topnotes".

The perfume composition of Example II(B) can be described as "a musk aroma with rich, natural vanilla bean and sweet undertones and dark chocolate topnotes".

The perfume composition of Example II(C) can be described as "a citrus aroma having rich, natural vanilla bean and sweet undertones with dark chocolate topnotes".

Each of the perfume formulations as a result of containing the compound having the structure:

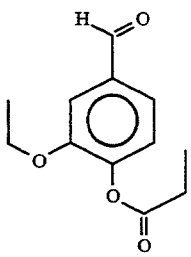

in the amount set forth, supra, and in the concentration set forth, supra, gives rise to non-discoloring perfume formulations.

EXAMPLE III

Preparation of Soap Composition

One hundred grams of soap chips are produced according to Example V of U.S. Pat. No. 4,058,487 issued on Nov. 15, 1977 the specification for which is incorporated by reference herein, as follows:

The sodium salt of an equal mixture of $C_{10}$–$C_{14}$ alkane sulfonates (95% active), 40 pounds, is dissolved in a mixture of 80 pounds of anhydrous isopropanol and 125 pounds of dionized water at 150° F. In this mixture is dissolved 10 pounds of partially hydrogenated coconut oil, fatty acids and 15 pounds of sodium mono-$C_{14}$-alkylmaleate. The pH of the solution is adjusted to 6.0 by the addition of a small amount of a 50% aqueous sodium hydroxide solution. The isopropanol is distilled off and the remaining aqueous solution is drum dried. The resulting solid actives are then blended in a chip mixture with 10 pounds of water, 0.2 pounds titanium hydroxide and 0.75 pounds of one of the materials set forth below:

TABLE I

| Perfume Ingredient | Perfume Profile |
|---|---|
| 2-Ethoxy-4-formyl phenyl ester of propionic acid having the structure: 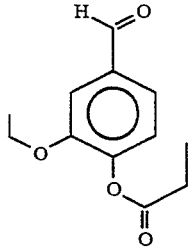 | A rich natural vanilla bean, sweet aroma with dark chocolate topnotes. |
| Perfume composition of Example II(A). | A magnolia aroma with rich, natural vanilla bean and sweet undertones and dark chocolate topnotes. |
| Perfume composition of Example II(B). | A musk aroma with rich, natural vanilla bean and sweet undertones and dark chocolate topnotes. |
| Perfume composition of Example II(C). | A citrus aroma having rich, natural vanilla bean and sweet undertones with dark chocolate topnotes. |

The chips are then plodded into logs, cut to size and finally stamped into bars, having a pH of approximately 6.9.

Each of the perfumed soaps of Table I above manifests an excellent characteristic aroma as indicated in Table I above. Furthermore, each of the perfume soaps is non-discoloring.

EXAMPLE IV

Preparation of A Detergent Composition

A total of 100 grams of a detergent powder prepared according to U.S. Pat. No. 4,058,472 and containing 5% by weight of the sodium salts of a mixture of sulfonated $C_{14}$–$C_{18}$ alkyl catechol as a surface active component, the mixture being 60 parts by weight of mono-$C_{14}$–$C_{18}$ alkyl catechol and 40 parts by weight of di-$C_{14}$–$C_{18}$ alkyl catechol, 35% of sodium tetrapyrophosphate, 30% of sodium silicate, 20% of sodium carbonate, 3% of sodium carboxymethyl cellulose and 7% of starch is mixed with 0.15 grams of one of the perfume ingredients of Table I of Example III, supra, until a substantially homogeneous composition is obtained. This composition has an excellent aroma as indicated according to Table I of Example III, supra.

EXAMPLE V

Preparation of Cosmetic Powder Compositions

A cosmetic powder is prepared by mixing in a ball mill 100 grams of talcum powder with 0.25 grams of one of the perfume materials of Table I of Example III, supra. Each of the cosmetic powders has an excellent aroma as set forth in Table I of Example III, supra.

EXAMPLE VI

Perfumed Liquid Detergents

Concentrated liquid detergents having aromas as set forth in Table I of Example III, supra, are prepared by adding 0.10%, 0.15% and 0.20% of each of the perfume ingredients of Table I of Example III, supra. They are prepared by adding and homogeneously mixing the appropriate quantity of perfume material in the liquid detergent. The detergents all possess aromas as set forth in Table I of Example III, supra.

EXAMPLE VII

Preparation of Cologne and Handkerchief Perfumes

Each of the compositions of Table I of Example III, supra, is incorporated into colognes at several concentrations, 2.0%, 2.5%, 3.0%, 3.5%, 4.0% and 5.0% in 70%, 75%, 80%, 85% and 90% aqueous ethanol; and into handkerchief perfumes at concentrations of 10%, 15%, 20% and 25% (in 80%, 85%, 90% and 95% aqueous ethanol). The use of each of the perfume ingredients as set forth in Table I of Example III, supra, affords distinctive aromas as set forth in Table I of Example III, supra.

EXAMPLE VIII

Preparation of A Composition

A total of 100 grams of a detergent powder (a nonionic detergent powder containing a proteolytic enzyme prepared according to Example I of Canadian Patent No. 985,190 issued on Mar. 9, 1976) is mixed with 0.15 grams of a perfume material set forth in Table I of Example III, supra, until a substantially homogeneous composition is obtained in each case. Each of the compositions has an excellent aroma as set forth in Table I of Example III, supra.

EXAMPLE IX

Utilizing the procedure of Example I at column 15 of U.S. Pat. No. 3,632,396 (which is hereby incorporated by reference into the instant specification), a nonwoven cloth substrate useful as a dryer-added fabric softening article of manufacture is prepared wherein the substrate, the substrate coating and the outer coating and the perfume material are as follows:
1. a water "dissolvable" paper ("Dissolvo Paper");
2. Adogen 448 (m.p. about 140° F.) as the substrate coating; and
3. an outer coating having the following formulation (m.p. about 150° F.):
   57%—$C_{20-22}$ HAPS
   22%—isopropyl alcohol
   20%—antistatic agent
   2.5%—of one of the perfume materials of Table I of Example III, supra.

A fabric softening composition prepared as set forth above having an aroma characteristic as set forth in Table I of Example III, supra, consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and an outer coating weight ratio of about 1:1 by weight of the substrate. The resulting aromas can be described as set forth in Table I of Example III, supra, and are imparted in pleasant manners to the head space in the dryer on operation thereof using said dryer-added fabric softening nonwoven fabric.

EXAMPLE X

Perfumed Polyethylene

Scented polyethylene pellets having a pronounced aroma as set forth in Table i of Example III, supra, are prepared as follows (in accordance with Example III of U.S. Pat. No. 3,505,432 which is incorporated by reference herein).

75 Pounds of polyethylene of a melting point of about 220° F. are heated to about 230° F. in a container as illustrated in FIGS. 1 and 2 of U.S. Pat. No. 3,505,432. 25 Pounds of one of the perfume materials of Table I of Example III, supra, are then quickly added to the liquified polyethylene, the lid is put in place and the agitating means are actuated. The temperature is maintained at about 225° F. and the mixing is continued for about 15 minutes. The valve is then opened to allow flow of the molten polyethylene enriched with the perfume containing material to exit through the orifices as indicated in FIGS. 1 and 2 of U.S. Pat. No. 3,505,432. The liquid falling through the orifices solidifies almost instantaneously upon impact with the moving cooled conveyor. Solid polyethylene beads or pellets having a pronounced aroma as set forth in Table I of Example III, supra, are thus formed. Analysis demonstrates that the pellets contain about 25% of the perfume substance of Table I of Example III, supra, so that almost no losses of the scenting substance occur. These pellets may be called master pellets. 50 Pounds of the perfume substance containing master pellets are then added to 1000 pounds of unscented polyethylene powder and the mass is heated to the liquid state. The liquid is molded into thin sheets or films. The sheets or films have a pronounced aroma as set forth in Table I of Example III, supra.

EXAMPLE XI

Scented Polypropylene

100 Pounds of polypropylene are heated to about 300° F. 30 Pounds of one of the aroma materials of Table I of Example III, supra, are added to the liquified polypropylene. The procedure is carried out in the apparatus of FIGS. 1 and 2 of U.S. Pat. No. 3,505,432. After mixing for about 8 minutes, the valve is opened to allow the exit of the polypropylene-scented material mixture whereby solid pellets having a pronounced aroma as set forth in Table I of Example III, supra, are formed on the conveyor. The pellets thus obtained are then admixed with about 20 times their weight of unscented polypropylene and the mixture is heated and molded into flat discs. The flat discs have a strong and pleasant aroma as set forth in Table I of Example III, supra.

EXAMPLE XII

A perfumed polymer is produced by admixing a microporous polymer produced according to one of Examples 194–236 of U.S. Pat. No. 4,247,498 (the disclosure of which is incorporated by reference herein), and applying a 0.5 mm/Hg. vacuum to the system. The resulting product is then compressed into pellets and molded into fragrance-emitting plastic objects, e.g., automobile dashboards.

What is claimed is:
1. 2-ethoxy-4-formyl phenyl ester of propionic acid having the structure:

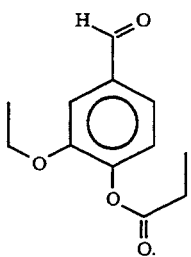

2. A process for augmenting or enhancing the aroma of a consumable material selected from the group consisting of perfume compositions, colognes and perfumed articles comprising the step of adding to said consumable material an aroma augmenting, imparting or enhancing quantity of 2-ethoxy-4-formyl phenyl ester of propionic acid defined according to c3laim 1.

3. The process of claim 2 wherein the consumable material is a perfume composition.

4. The process of claim 2 wherein the consumable material is a cologne.

5. The process of claim 2 wherein the consumable material is a perfumed article and the perfumed article is a solid or liquid anionic, cationic, nonionic or zwitterionic detergent.

6. The process of claim 2 wherein the consumable material is a perfumed article and the perfumed article is a perfumed polymer.

7. The process of claim 2 wherein the consumable material is a perfumed article and the perfumed article is a fabric softener composition or drier-added fabric softener article.

8. A perfume composition consisting essentially of a perfume base and intimately admixed therewith in a perfume imparting, augmenting or enhancing quantity or concentration 2-ethoxy-4-formyl phenyl ester of propionic acid defined according to claim 1.

9. A solid or liquid anionic, cationic, nonionic or zwitterionic detergent composition consisting essentially of a solid or liquid anionic, cationic, nonionic or zwitterionic detergent base and intimately admixed therewith an aroma augmenting, enhancing or imparting quantity or concentration of the 2-ethoxy-4-formyl phenyl ester of propionic acid defined according to claim 1.

10. A perfumed polymer consisting essentially of a microporous polymer and containing in the interstices thereof an aroma imparting, augmenting or enhancing quantity of the 2-ethoxy-4-formyl phenyl ester of propionic acid of claim 1.

11. A perfumed polymer consisting essentially of a microporous polymer and contained in the interstices thereof an aroma imparting, augmenting or enhancing quantity of the perfume composition of claim 8.

12. A cologne consisting essentially of water, ethanol and the 2-ethoxy-4-formyl phenyl ester of propionic acid defined according to claim 1.

* * * * *